United States Patent [19]
Campbell et al.

[11] Patent Number: 5,752,934
[45] Date of Patent: May 19, 1998

[54] BALLOON CATHETER DEVICE

[75] Inventors: Carey V. Campbell; Alvaro J. Laguna, both of Flagstaff, Ariz.

[73] Assignee: W. L. Gore & Associates, Inc., Newark, Del.

[21] Appl. No.: 532,905

[22] Filed: Sep. 18, 1995

[51] Int. Cl.$^6$ .................................................. A61M 29/00
[52] U.S. Cl. ...................................................... 604/96; 606/194
[58] Field of Search ............................. 604/96, 101, 264, 604/280; 606/194

[56] References Cited

U.S. PATENT DOCUMENTS

| | | |
|---|---|---|
| 4,003,382 | 1/1977 | Dyke . |
| 4,106,509 | 8/1978 | McWhorter . |
| 4,194,041 | 3/1980 | Gore et al. . |
| 4,279,245 | 7/1981 | Takagi et al. . |
| 4,304,010 | 12/1981 | Mano . |
| 4,403,612 | 9/1983 | Fogarty . |
| 4,443,511 | 4/1984 | Worden et al. . |
| 4,573,966 | 3/1986 | Weikl et al. . |
| 4,613,544 | 9/1986 | Burleigh . |
| 4,619,641 | 10/1986 | Schanzer . |
| 4,637,396 | 1/1987 | Cook . |
| 4,650,466 | 3/1987 | Luther . |
| 4,702,252 | 10/1987 | Brooks et al. . |
| 4,706,670 | 11/1987 | Andersen et al. . |
| 4,764,560 | 8/1988 | Mitchell . |
| 4,816,339 | 3/1989 | Tu et al. . |
| 4,832,688 | 5/1989 | Sagae et al. . |
| 4,896,669 | 1/1990 | Bhate et al. . |
| 4,946,464 | 8/1990 | Pevsner . |
| 4,955,899 | 9/1990 | Della Corna et al. . |
| 5,071,609 | 12/1991 | Tu et al. . |
| 5,087,244 | 2/1992 | Wolinsky et al. . |
| 5,112,304 | 5/1992 | Barlow et al. . |
| 5,116,318 | 5/1992 | Hillstead . |
| 5,152,782 | 10/1992 | Kowligi et al. . |
| 5,192,296 | 3/1993 | Bhate et al. . |
| 5,201,706 | 4/1993 | Noguchi et al. . |
| 5,213,576 | 5/1993 | Abiuso et al. . |
| 5,236,659 | 8/1993 | Pinchuk et al. . |
| 5,254,090 | 10/1993 | Lombardi et al. . |
| 5,256,143 | 10/1993 | Miller et al. . |
| 5,286,254 | 2/1994 | Shapland et al. . |
| 5,290,306 | 3/1994 | Trotta et al. . |
| 5,348,538 | 9/1994 | Wang et al. . |
| 5,358,516 | 10/1994 | Myers et al. . |
| 5,403,340 | 4/1995 | Wang et al. . |
| 5,415,636 | 5/1995 | Forman . |
| 5,425,710 | 6/1995 | Khair et al. . |
| 5,429,605 | 7/1995 | Richling . |
| 5,456,661 | 10/1995 | Narciso . |
| 5,458,568 | 10/1995 | Racchini et al. . |
| 5,466,252 | 11/1995 | Soukup et al. . |
| 5,470,313 | 11/1995 | Crocker et al. . |
| 5,478,320 | 12/1995 | Trotta et al. . |
| 5,490,839 | 2/1996 | Wang et al. . |

(List continued on next page.)

FOREIGN PATENT DOCUMENTS

| | | |
|---|---|---|
| 372088 | 6/1990 | European Pat. Off. . |
| 96/14895 | 5/1996 | WIPO . |
| 9702791 | 1/1997 | WIPO . |

OTHER PUBLICATIONS

Dillon M E, Silicone and Poly (tetraFluoroethylene) Interpenetrating Polymer Networks. 1994 American Chemical Society.

*Primary Examiner*—Michael Powell Buiz
*Assistant Examiner*—N. Kent Gring
*Attorney, Agent, or Firm*—Wayne D. House

[57] ABSTRACT

Balloon catheters having the strength and maximum inflated diameter characteristics of an angioplasty balloon and having the recovery characteristics during deflation of an elastic embolectomy balloon. The balloon catheter can be made in very small sizes and has a lubricous and chemically inert outer surface. The balloon catheter is easy to navigate through tortuous passageways, is capable of rapid inflation and deflation and has high burst strengths. Balloon covers having these same characteristics are also described for use with conventional embolectomy balloons or angioplasty balloons.

38 Claims, 5 Drawing Sheets

U.S. PATENT DOCUMENTS

| | | |
|---|---|---|
| 5,496,276 | 3/1996 | Wang et al. . |
| 5,498,238 | 3/1996 | Shapland et al. . |
| 5,499,973 | 3/1996 | Saab ............................................ 604/96 |
| 5,499,980 | 3/1996 | Euteneuer . |
| 5,499,995 | 3/1996 | Teirstein . |
| 5,500,180 | 3/1996 | Anderson et al. . |
| 5,500,181 | 3/1996 | Wang et al. . |
| 5,512,051 | 4/1996 | Wang et al. . |
| 5,519,172 | 5/1996 | Spencer et al. . |
| 5,527,282 | 6/1996 | Segal . |
| 5,529,820 | 6/1996 | Nomi et al. . |
| 5,613,979 | 3/1997 | Trotta et al. . |
| 5,620,649 | 4/1997 | Trotta . |
| 5,641,373 | 6/1997 | Shannon et al. . |

BALLOON CATHETER DEVICE

FIELD OF THE INVENTION

The present invention relates to balloon catheters used in a variety of surgical procedures and to balloon covers for use with balloon catheters.

BACKGROUND OF THE INVENTION

Balloon catheters of various forms are commonly employed in a number of surgical procedures. These devices comprise a thin catheter tube that can be guided through a body conduit of a patient such as a blood vessel and a distensible balloon located at the distal end of the catheter tube. Actuation of the balloon is accomplished through use of a fluid filled syringe or similar device that can inflate the balloon by filling it with fluid (e.g., water or saline solution) to a desired degree of expansion and then deflate the balloon by withdrawing the fluid back into the syringe.

In use, a physician will guide the balloon catheter into a desired position and then expand the balloon to accomplish the desired result (e.g., clear a blockage, or install or actuate some other device). Once the procedure is accomplished, the balloon is then deflated and withdrawn from the blood vessel.

There are two main forms of balloon catheter devices. Angioplasty catheters employ a balloon made of relatively strong but generally inelastic material (e.g., polyester) folded into a compact, small diameter cross section. These relatively stiff catheters are used to compact hard deposits in vessels. Due to the need for strength and stiffness, these devices are rated to high pressures, usually up to about 8 to 12 atmospheres depending on rated diameter. They tend to be self-limiting as to diameter in that they will normally distend up to the rated diameter and not distend appreciably beyond this diameter until rupture due to over-pressurization. While the inelastic material of the balloon is generally effective in compacting deposits, it tends to collapse unevenly upon deflation, leaving a flattened, wrinkled bag, substantially larger in cross section than the balloon was when it was originally installed. Because of their tendency to assume a flattened cross section upon inflation and subsequent deflation, their deflated maximum width tends to approximate a dimension corresponding to one-half of the rated diameter times π. This enlarged, wrinkled bag may be difficult to remove, especially from small vessels. Further, because these balloons are made from inelastic materials, their time to complete deflation is inherently slower than elastic balloons.

By contrast, embolectomy catheters employ a soft, very elastic material (e.g., natural rubber latex) as the balloon. These catheters are employed to remove soft deposits, such as thrombus, where a soft and tacky material such as latex provides an effective extraction means. Latex and other highly elastic materials generally will expand continuously upon increased internal pressure until the material bursts. As a result, these catheters are generally rated by volume (e.g., 0.3 cc) in order to properly distend to a desired size. Although relatively weak, these catheters do have the advantage that they tend to readily return to their initial size and dimensions following inflation and subsequent deflation.

While balloon catheters are widely employed, currently available devices experience a number of shortcomings. First, as has been noted, the strongest materials for balloon construction tend to be relatively inelastic. The flattening of catheter balloons made from inelastic materials that occurs upon inflation and subsequent deflation makes extraction and navigation of a deflated catheter somewhat difficult. Contrastly, highly elastic materials tend to have excellent recovery upon deflation, but are not particularly strong when inflated nor are they self-limiting to a maximum rated diameter regardless of increasing pressure. This severely limits the amount of pressure that can be applied with these devices. It is also somewhat difficult to control the inflated diameter of these devices.

Second, in instances where the catheter is used to deliver some other device into the conduit, it is particularly important that a smooth separation of the device and the catheter occur without interfering with the placement of the device. Neither of the two catheter devices described above is ideal in these instances. A balloon that does not completely compact to its original size is prone to snag the device causing placement problems or even damage to the conduit or balloon. Similarly, the use of a balloon that is constructed of tacky material will likewise cause snagging problems and possible displacement of the device. Latex balloons are generally not used for device placement in that they are considered to have inadequate strength for such use. Accordingly, it is a primary purpose of the present invention to create a catheter balloon that is small and slippery for initial installation, strong for deployment, and returns to its compact size and dimensions for ease in removal and further navigation following deflation. It is also believed desirable to provide a catheter balloon that will remain close to its original compact pre-inflation size even after repeated cycles of inflation and deflation. Other primary purposes of the present invention are to strengthen elastic balloons, to provide them with distension limits and provide them with a lubricous outer surface. The term "deflation" herein is used to describe a condition subsequent to inflation. "Pre-inflation" is used to describe the condition prior to initial inflation.

SUMMARY OF THE INVENTION

The present invention is an improved balloon catheter device for use in a variety of surgical procedures. The balloon catheter device of the present invention comprises a catheter tube having a continuous lumen connected to an inflatable and deflatable balloon at one end of the catheter tube. The catheter tube may have additional lumens provided for other purposes. The balloon can have a burst strength equal to or greater than that of conventional PTA catheter balloons. The balloon also has a maximum inflation diameter in a similar fashion to conventional PTA catheter balloons. The inventive balloon offers the recovery characteristics of a latex balloon that when deflated is of about the same maximum diameter as it was prior to inflation. This allows the inventive balloon to be withdrawn following deflation more easily than conventional PTA balloons which assume a flattened, irregular cross section following deflation and so have a deflated maximum diameter much larger than the pre-inflation maximum diameter. The balloon also has a smooth and lubricous surface which also aids in insertion and withdrawal. The inventive balloon possesses all of the above attributes even when made in small sizes heretofore commercially unavailable in balloon catheters. The small sizes are anticipated to allow the use of balloons inserted through small, tortuous paths in applications such as those involving the brain, liver or kidney. The balloon portion of the inventive balloon catheter device is made primarily of porous expanded polytetrafluoroethylene (hereinafter PTFE). The balloon may be made from the materials described below as a complete, stand-alone balloon or alternatively may be made as a cover for either conventional polyester PTA balloons or for latex embolectomy balloons. The use of the balloon cover of the present invention provides the covered balloon, regardless of type, with the best features of PTA balloons and renders viable the use of elastic balloons for PTA procedures. That is to say, the covered balloon will have high burst strength, a predetermined maximum diameter, the ability to recover to substantially its pre-inflation size following deflation, and a lubricous exterior surface. The balloon cover substantially reduces the risk of rupture of an elastic balloon. Further, if rupture of the underlying balloon should occur, the presence of the balloon cover may serve to contain the fragments of the ruptured balloon. Still further, the inventive balloon and balloon cover can increase the rate of deflation of PTA balloons thereby reducing the time that the inflated balloon occludes the conduit in which it resides.

DETAILED DESCRIPTION OF THE INVENTION

The catheter balloon and catheter balloon cover of the present invention are preferably made from porous PTFE films having a microstructure of interconnected fibrils. These films are made as taught by U.S. Pat. Nos. 3,953,566 and 4,187,390, both of which are herein incorporated by reference.

Figures 1A, 1B, 1C, 2:
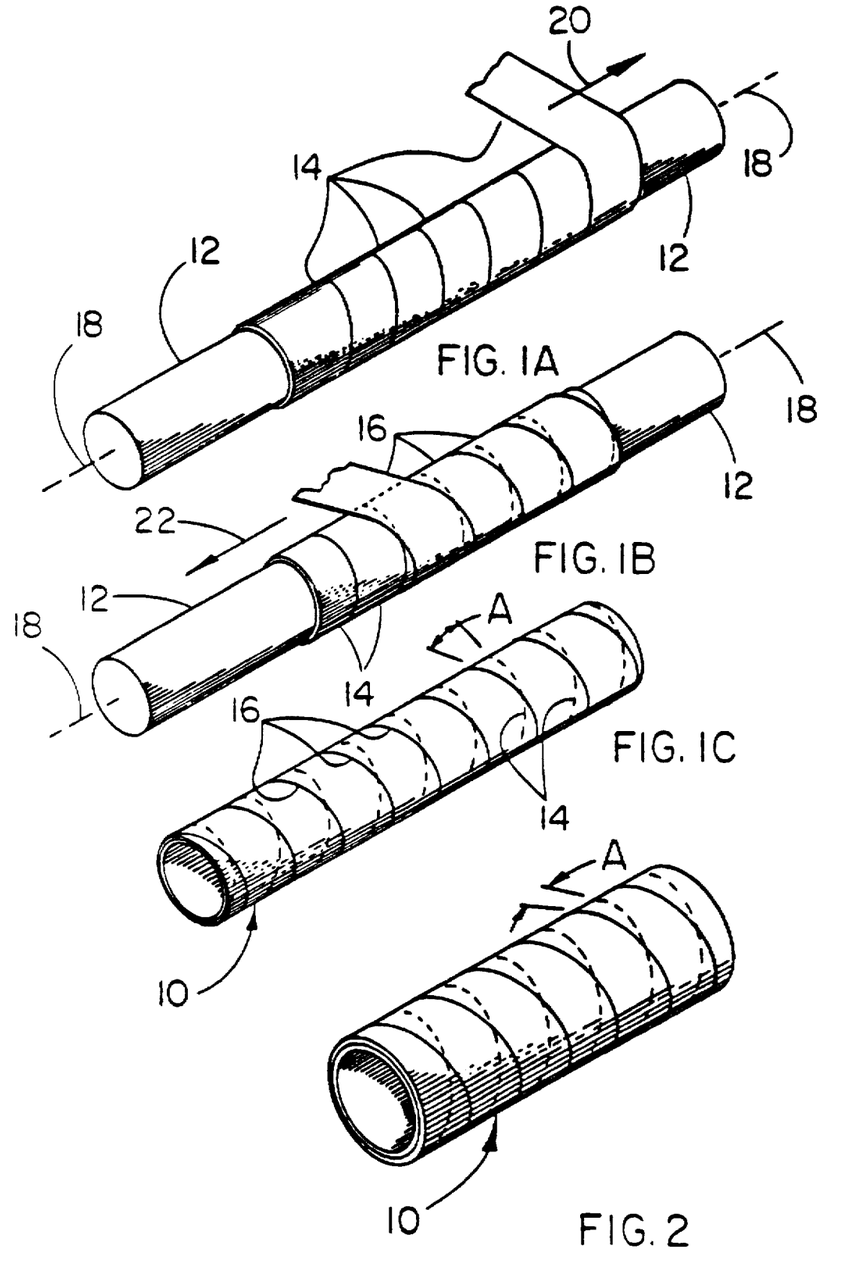
FIGS. 1A, 1B and 1C are perspective views describing manufacture of the tubular component forming the balloon or balloon cover of the present invention.
FIG. 2 is a perspective view describing the tubular component as it appears when inflated.

To form the balloon or balloon cover, both of which are made in the shape of a tube, a thin, porous PTFE film of the type described above is slit into relatively narrow lengths. The slit film is helically wrapped onto the surface of a mandrel in two opposing directions, thereby forming a tube of at least two layers. FIGS. 1A, 1B and 1C describe this procedure. FIG. 1A shows the first layer 14 of porous PTFE film helically wrapped over the mandrel 12 with the traverse direction of the wrap applied in a first direction 20 parallel to the longitudinal axis 18. FIG. 1B describes the application of the second layer of porous PTFE film 16 helically wrapped over the top of the first layer 14, wherein second layer 16 is wrapped in a second direction 22 parallel to longitudinal axis 18 and opposite to the first direction 20.

Preferably both layers 14 and 16 are wrapped with the same pitch angle measured with respect to the longitudinal axis but measured in opposite directions. If, for example, film layers 14 and 16 are applied at pitch angles of 70° measured from opposite directions with respect to longitudinal axis 18, then included angle A between both 70° pitch angles is 40°.

More than two layers of helically wrapped film may be applied. Alternate layers of film should be wrapped from opposing directions and an even number of film layers should be used whereby an equal number of layers are applied in each direction.

Following completion of film wrapping, the helically wrapped mandrel is placed into an oven for suitable time and temperature to cause adjacent layers to heat-bond together. After removal from the oven and subsequent cooling, the resulting film tube may be removed from the mandrel. The film tube is next placed over the balloon, tensioned longitudinally and affixed in place over the balloon.

During use, the inflated balloon or balloon cover 10 of the present invention has an increased diameter which results in included angle A being substantially reduced as shown by FIG. 2. The balloon or balloon cover thus reaches its pre-determined diametrical limit as included angle A approaches zero.

The inventive balloon or balloon cover 10 is reduced in diameter following deflation by one of two ways. First, tension may be applied to the balloon or balloon cover parallel to longitudinal axis 18 to cause it to reduce in diameter following deflation to the form described by FIG. 1C. The application of tension is necessary if low profile is desired. Alternatively, a layer of elastomer, applied to the luminal surface of the balloon 10 and allowed to cure prior to use of the balloon, will cause the balloon to retract to substantially its pre-inflation size shown by FIG. 1C following deflation. The elastomer may take the form of a coating of elastomer applied directly to the luminal surface of the balloon or balloon cover 10, or an elastomeric balloon such as a latex balloon may be adhered to the luminal surface of the inventive balloon 10 by the use of an elastomeric adhesive.

Figure 3A:
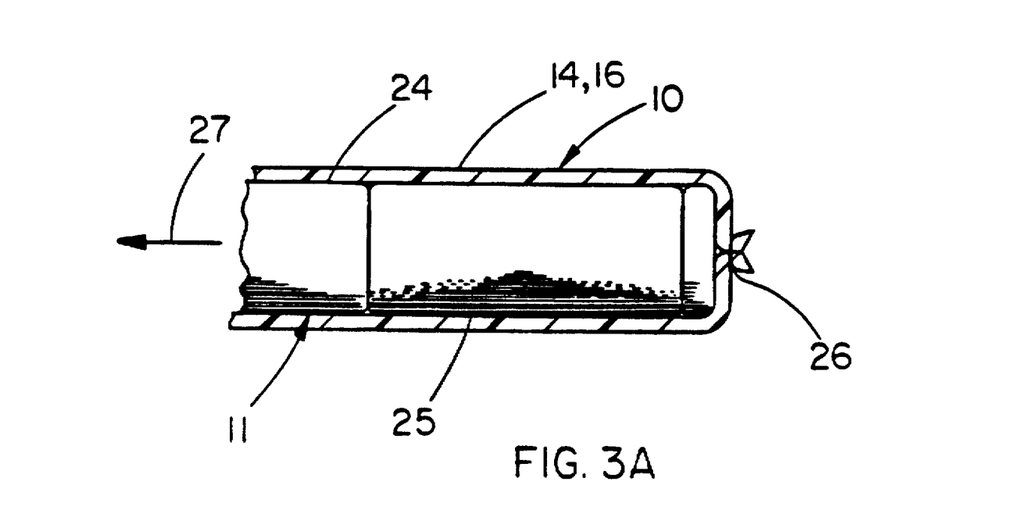
FIGS. 3A and 3B describe cross sectional views of a balloon cover of the present invention without elastomer.
Figure 3B:
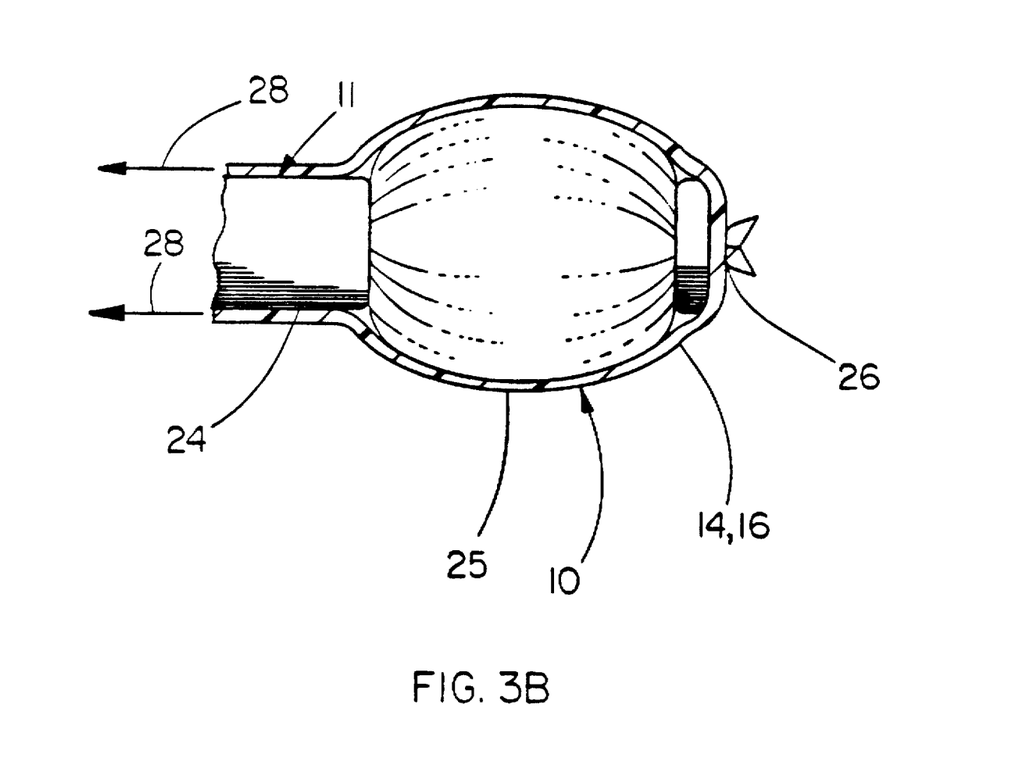

FIG. 3A describes a cross sectional view of a balloon cover 10 of the present invention in use with a conventional balloon catheter of either the angioplasty or embolectomy type. The figure describes a balloon cover without an elastomeric luminal coating. The balloon cover 10 is closed at distal end 26 of the balloon catheter 11. Balloon cover 10 extends in length part of the way to the proximal end 27 of balloon catheter 11 whereby balloon cover 10 completely covers catheter balloon 25 and at least a portion of the catheter 11. FIG. 3B describes the same balloon catheter 11 with catheter balloon 25 in an inflated state. Layers 14 and 16 of balloon cover 10 allow the cover to increase in diameter along with catheter balloon 25. During or following deflation of catheter balloon 25, tension is applied to the balloon cover 10 at the proximal end 27 of balloon catheter 11 as shown by arrows 28, thereby causing balloon cover 10 to reduce in diameter and substantially return to the state described by FIG. 3A.

Figure 4A:
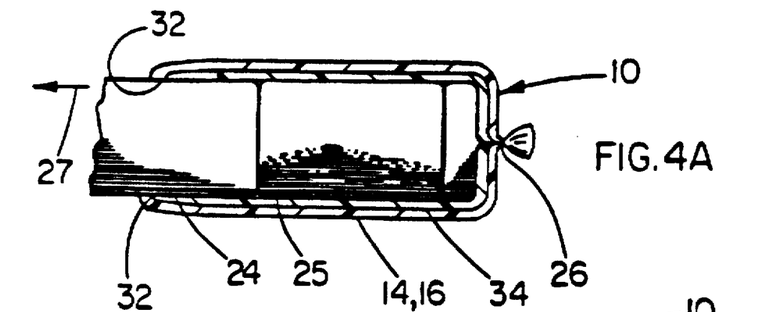
FIGS. 4A and 4B describe cross sectional views of a balloon cover of the present invention incorporating a layer of elastomer.
Figure 4B:
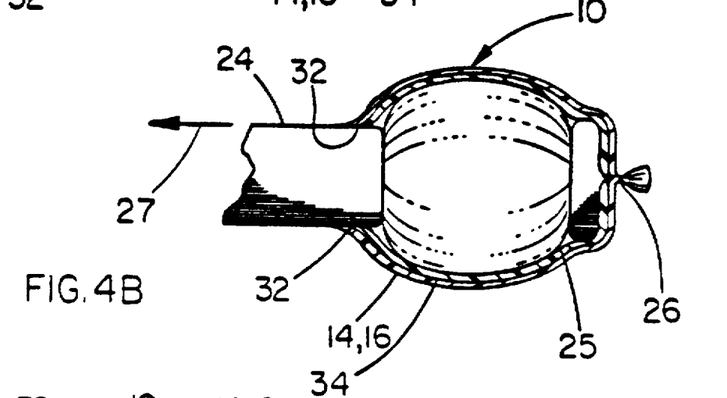

FIG. 4A describes a cross sectional view of a balloon cover 10 of the present invention wherein the balloon cover 10 has a liquid-tight layer of elastomer 34 applied to the inner surface of helically wrapped porous PTFE film layers 14 and 16. Balloon cover 10 is closed at distal end 26. The figure describes a ligated closure, such as by a thread or filament, however, other suitable closing means may be used. Proximal end 27 of balloon cover 10 is affixed to the distal end 32 of catheter 24. Balloon 25 may be of either the angioplasty or embolectomy type. If an elastomeric embolectomy balloon is used, it is preferred that the cover be adhered to the balloon by the use of an elastomeric adhesive to liquid-tight layer of elastomer 34. During inflation of balloon 25 as shown by FIG. 4B, helically wrapped porous PTFE film layers 14 and 16 and liquid-tight elastomer layer 34 increase in diameter along with balloon 25. During subsequent deflation, liquid-tight elastomer layer 34 causes helically wrapped porous PTFE film layers 14 and 16 to reduce in diameter as described previously, thereby returning substantially to the state described by FIG. 4A.

Figures 5A, 5B:
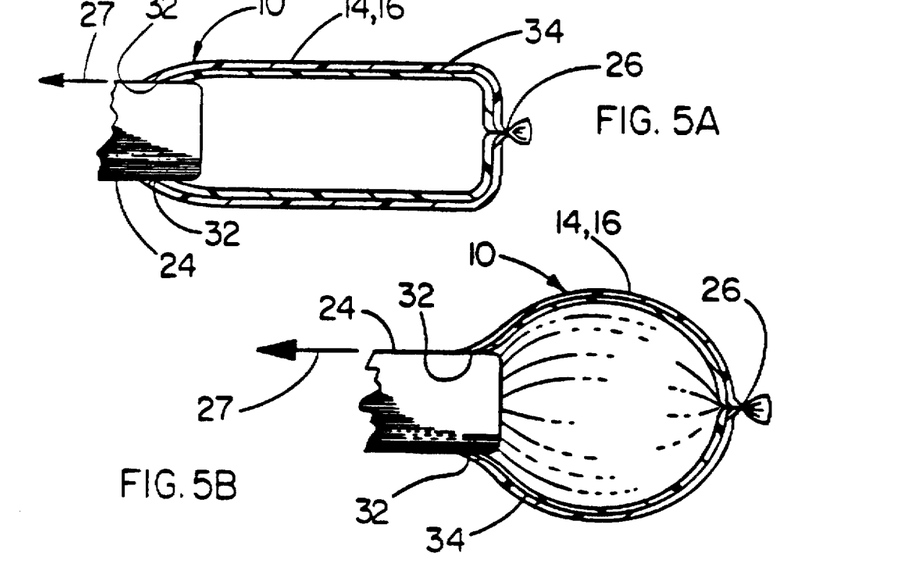
FIGS. 5A and 5B describe cross sectional views of a catheter balloon of the present invention having the same material construction as the balloon cover of FIGS. 4A and 4B.

FIGS. 5A and 5B describe cross sectional views of a catheter balloon 10 made in the same fashion as the balloon cover described by FIGS. 4A and 4B. The presence of liquid-tight elastomer layer 34 allows this construction to function as an independent balloon 42 as described previously without requiring a conventional angioplasty or embolectomy balloon.

Figure 6A:
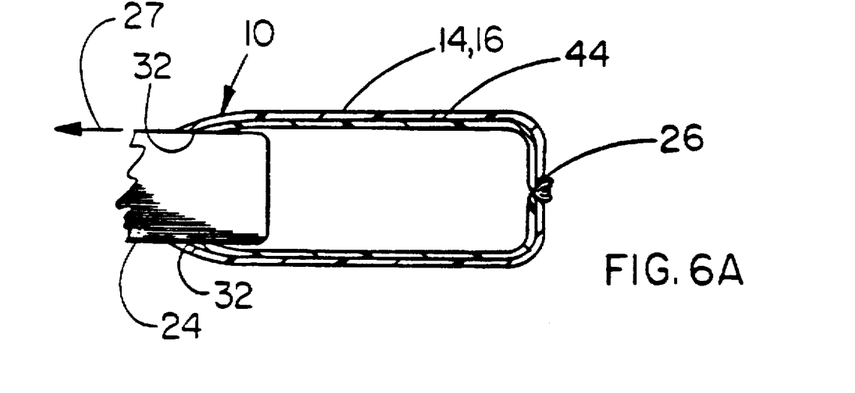
FIGS. 6A, 6B and 6C describe cross sectional views of a catheter balloon of the type described by FIGS. 5A and 5B using a non-elastomeric material in place of the layer of elastomer.
Figure 6B:
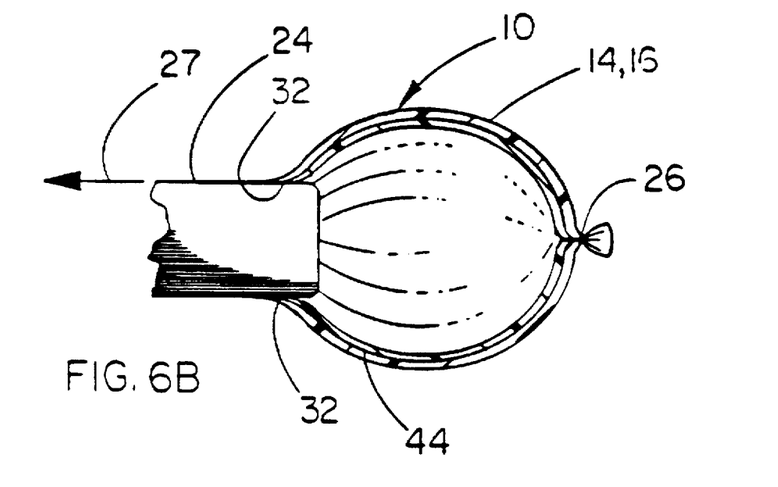
Figure 6C:
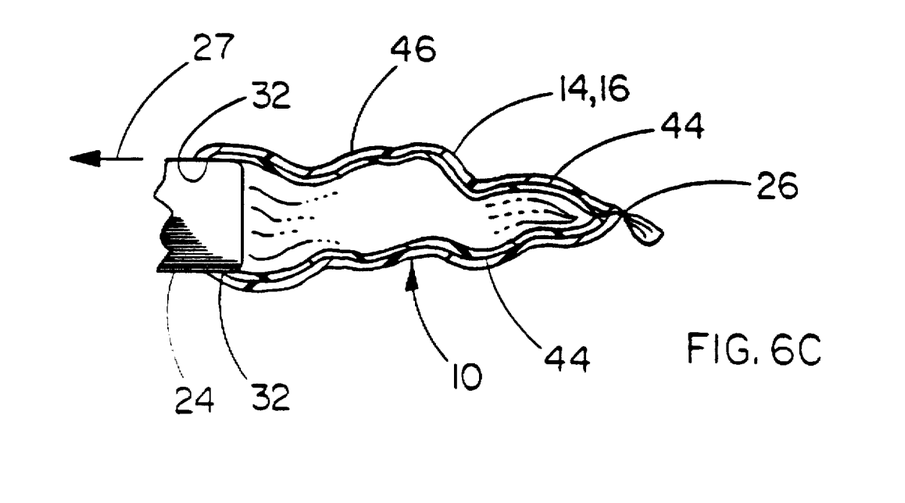

FIGS. 6A, 6B and 6C describe cross sectional views of an alternative embodiment of the catheter balloon 10 of the present invention. According to this embodiment helically wrapped porous PTFE film layers 14 and 16 are provided with a luminal coating 44 which is liquid-tight but is not elastomeric. The resulting balloon behaves in the fashion of a conventional angioplasty balloon but offers the advantages of a lubricous and chemically inert exterior surface. FIG. 6A describes the appearance of the balloon prior to inflation. FIG. 6B describes the balloon in an inflated state. As shown by FIG. 6C, following deflation, collapsed balloon 46 has a somewhat wrinkled appearance and an irregular transverse cross section in the same fashion as a conventional angioplasty balloon made from polyester or similar inelastic material.

It is also anticipated that the balloon and balloon cover of the present invention may be provided with an additional reinforcing mesh or braid on the exterior or interior surface of the balloon (or balloon cover), or more preferably between layers of the film whereby the mesh or braid is in the middle.

Alternatively, a mesh or braid of PTFE may be used as a balloon cover without including a continuous tube. A continuous tube does not include openings through its wall as does a conventional mesh or braid.

Figure 7:
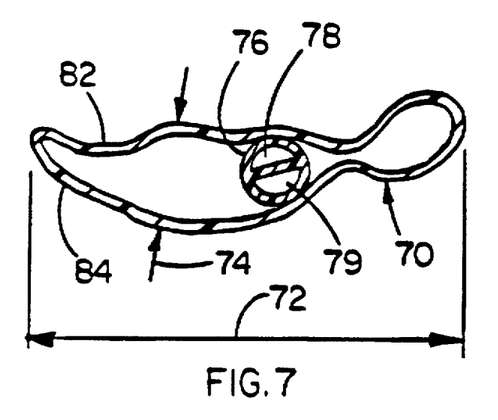
FIG. 7 describes a transverse cross section taken at the center of the length of a flattened, deflated angioplasty balloon which describes how the compaction efficiency ratio of the deflated balloon is determined.

The following examples describe in detail the construction of various embodiments of the balloon cover and catheter balloon of the present invention. Evaluation of these balloons is also described in comparison to conventional angioplasty and embolectomy balloons. FIG. 7 is provided as a description of the maximum dimension 72 and minimum dimension 74 (taken transversely to the longitudinal axis of the balloon) of a flattened, deflated angioplasty balloon 70 wherein the figure describes a transverse cross section of a typical flattened angioplasty balloon. The transverse cross section shown is meant to describe a typical deflated, flattened inelastic angioplasty balloon 70 having a somewhat irregular shape. Balloon 70 includes a catheter tube 76 having a guidewire lumen 78 and a balloon inflation lumen 79 and two opposing sides 82 and 84 of balloon 70. Maximum dimension 72 may be considered to be the maximum width of the flattened balloon 70 while minimum dimension 74 may be considered to be the maximum thickness across the two opposing sides 82 and 84 of the flattened balloon 70. All balloon and catheter measurements are expressed in terms of dimensions even if the shape is substantially circular.

EXAMPLE 1

This example illustrates the use of a balloon cover of the present invention over a commercially available angioplasty balloon. The balloon cover provides a means of returning the angioplasty balloon close to its original compact geometry after inflation and subsequent deflation, as well as providing the known chemical inertness and low coefficient of friction afforded by PTFE.

The balloon used was a MATCH 35® Percutaneous Transluminal Angioplasty (PTA) Catheter model number B508-412, manufactured by SCHNEIDER (Minneapolis, Minn.). This balloon when measured immediately after being removed from the protective sheath provided by the manufacturer had a minimum dimension of 2.04 mm and a maximum dimension of 2.42 mm. These measurements were taken from approximately the center of the balloon, as defined by the midpoint between the circumferentially-oriented radiopaque marker bands located at both ends of the balloon. A Lasermike model 183, manufactured by Lasermike, (Dayton, Ohio) was used to make the measurements while the balloon was rotated about its longitudinal axis. The shaft onto which the balloon was attached had a minimum dimension of 1.74 mm and a maximum dimension of 1.77 mm measured adjacent to the point of balloon attachment closest to the center of the length of the shaft. The balloon, when inflated to 8 atmospheres internal water pressure, had a minimum dimension of 8.23 mm and a maximum dimension of 8.25 mm at the center of the length of the balloon. When deflated by removing the entire volume of water introduced during the 8 atmosphere pressurization, the balloon at its midlength, had a minimum dimension of 1.75 mm, and a maximum dimension of 11.52 mm as measured using Mitutoyo digital caliper model CD-6"P. Upon completion of the measurements the balloon portion of the PTA catheter was carefully repackaged into the protective sheath.

The inventive balloon cover was made from a length of porous PTFE film made as described above cut to a width of 2.5 cm. The film thickness was approximately 0.02 mm, the density was 0.2 g/cc, and the fibril length was approximately 70μ. Thickness was measured using a Mitutoyo snap gauge model 2804-10 and density was calculated based on sample dimensions and mass. Fibril length of the porous PTFE films used to construct the examples was estimated from scanning electron photomicrographs of an exterior surface of film samples.

This film was helically wrapped onto the bare surface of an 8 mm diameter stainless steel mandrel at an angle of approximately 70° with respect to the longitudinal axis of the mandrel so that about 5 overlapping layers of film cover the mandrel. Following this, another 5 layers of the same film were helically wrapped over the first 5 layers at the same pitch angle with respect to the longitudinal axis, but in the opposite direction. The second 5 layers were therefore also oriented at an approximate angle of 70°, but measured from the opposite end of the axis in comparison to the first 5 layers. Following this, another 5 layers of the same film were helically wrapped over the first and second 5 layers at the same bias angle with respect to the longitudinal axis as the first 5 layers, and then another 5 layers of the same film were helically wrapped over the first, second, and third 5 layers at the same bias angle with respect to the longitudinal axis as the second 5 layers. This resulted in a total of about 20 layers of helically wrapped film covering the mandrel.

The film-wrapped mandrel was then placed into an air convection oven set at 380° C. for 10 minutes to heat bond the layers of film, then removed and allowed to cool. The resulting 8 mm inside diameter film tube formed from the helically wrapped layers was then removed from the mandrel and one end was ligated onto a self-sealing injection site (Injection Site with Luer Lock manufactured by Baxter Healthcare Corporation, Deerfield, Ill.). A hole was created through the injection site, and the balloon end of the previously measured PTA catheter was passed through this hole, coaxially fitting the film tube over the balloon portion as well as a portion of the shaft of the PTA catheter. The film tube was approximately 25 cm in length. With the film tube over the PTA catheter and attached to the injection site, tension was applied manually to the free end of the film tube while the injection site was held fixed, causing the film tube to reduce in diameter and fit snugly onto the underlying segment of PTA catheter. Next, the film tube was ligated at the distal end of the PTA catheter shaft so that the balloon cover remained taut and snugly fit.

At this point the now covered balloon was measured in a deflated state. The minimum dimension was found to be 2.04 mm and the maximum dimension 2.42 mm. As before, these measurements were taken from approximately the center of the balloon, as defined by the midpoint between the radiopaque marker bands, and a Lasermike model 183, manufactured by Lasermike, (Dayton, Ohio) was used to make the measurements. The balloon, when inflated to 8 atmospheres internal water pressure had a minimum dimension of 7.93 mm and a maximum dimension of 8.06 mm at the center of the balloon. When deflated by removing the entire volume of water introduced during the 8 atmosphere pressurization, the balloon at its midlength, had a minimum dimension of 1.92 mm and a maximum dimension of 11.17 mm. Next, tension was manually applied to the injection site causing the balloon cover to reduce the size of the underlying balloon, particularly along the plane of the 11.17 mm measurement taken previously. After the application of tension the covered balloon was measured again, and the minimum and maximum dimensions were found as 3.43 and 3.87 mm respectively.

This example shows that the balloon cover can be used effectively to compact a PTA balloon which was inflated and subsequently deflated to approximately the geometry of the balloon in an unused state. The measurements taken on the balloon (in both the uncovered and covered states) after inflation and subsequent deflation show that rather than undergoing a uniform circular compaction, the balloon tended to flatten. This flattening can be quantified by calculating the ratio of the minimum dimension to the maximum dimension measured after inflation and subsequent deflation. This ratio is defined as the compaction efficiency ratio. Note that a circular cross section yields a compaction efficiency ratio of unity. For this example, the uncovered balloon had a compaction efficiency ratio of 1.75÷11.52 or 0.15. The balloon, after being provided with the inventive balloon cover, had a compaction efficiency ratio of 3.43÷3.87 or 0.89. Additionally, the ratio of the maximum dimension prior to any inflation, to the maximum dimension after inflation and subsequent deflation, is defined as the compaction ratio. A balloon which has the same maximum dimension prior to any inflation, and after inflation and subsequent deflation, has a compaction ratio of unity. For this example, the uncovered balloon had a compaction ratio of 2.42÷11.52 or 0.21. The balloon, after being provided with the inventive balloon cover, had a compaction ratio of 2.63÷3.87 or 0.68.

EXAMPLE 2

This example illustrates the use of a balloon cover over a commercially available latex embolectomy balloon. The balloon cover provides a defined limit to the growth of the embolectomy balloon, a substantial increase in burst strength, and the known chemical inertness and low coefficient of friction afforded by PTFE.

The balloon used was a Fogarty® Thru-Lumen Embolectomy Catheter model 12TL0805F manufactured by Baxter Healthcare Corporation (Irvine, Calif.). This natural rubber latex balloon when measured immediately after being removed from the protective sheath provided by the manufacturer had a minimum dimension of 1.98 mm and a maximum dimension of 2.02 mm. These measurements were taken from approximately the center of the balloon, as defined by the midpoint between the radiopaque marker bands. A Lasermike model 183, manufactured by Lasermike, (Dayton, Ohio) was used to make the measurements while the balloon was rotated about its longitudinal axis. The shaft onto which the balloon was attached had a minimum dimension of 1.64 mm and a maximum dimension of 1.68 mm measured adjacent to the point of balloon attachment closest to the center of the length of the shaft. The balloon, when filled with 0.8 cubic centimeters of water had a minimum dimension of 10.71 mm and a maximum dimension of 10.77 mm at the center of the balloon. When deflated by removing the entire volume of water introduced, the balloon at its midlength, had a minimum dimension of 1.97 mm and a maximum dimension of 2.04 mm. The balloon when tested using a hand-held inflation syringe had a burst strength of 60 psi.

Another embolectomy catheter of the same type was covered using a porous PTFE film tube made as described in Example 1. The method used to cover the embolectomy catheter was the same as that used to cover the PTA catheter in Example 1.

At this point, the now covered balloon was measured in a pre-inflated state. The minimum dimension was found to be 2.20 mm and the maximum dimension 2.27 mm. As before, these measurements were taken from approximately the center of the balloon, as defined by the midpoint between the radiopaque marker bands, and a Lasermike model 183, manufactured by Lasermike (Dayton, Ohio) was used to make the measurements. The balloon, when filled with 0.8 cubic centimeters of water had a minimum dimension of 8.29 mm and a maximum dimension of 8.34 mm at midlength. When deflated by removing the entire volume of water introduced, the balloon at its midlength, had a minimum dimension of 3.15 mm and a maximum dimension of 3.91 mm. Next, tension was manually applied to the injection site causing the balloon cover to reduce in size. After the application of tension the covered balloon was measured again, and the minimum and maximum dimensions were found as 2.95 and 3.07 mm respectively. The covered balloon was determined to have a burst strength of 188 psi, failing solely due the burst of the underlying embolectomy balloon. The inventive balloon cover exhibited no indication of rupture.

This example shows that the inventive balloon cover effectively provides a limit to the growth, and a substantial increase in the burst strength of an embolectomy balloon. The measurements taken on the uncovered balloon show that when filled with 0.8 cubic centimeters of water the balloon reached a maximum dimension of 10.77 mm. Under the same test conditions, the covered balloon reached a maximum dimension of 8.34 mm. The burst strength of the uncovered balloon was 60 psi while the burst strength of the covered balloon was 188 psi when inflated until rupture using a hand-operated liquid-filled syringe. This represents more than a three fold increase in burst strength.

EXAMPLE 3

This example illustrates the use of a composite material in a balloon application. A balloon made from the composite material described below exhibits a predictable inflated diameter, high strength, exceptional compaction ratio and compaction efficiency ratio, as well as the known chemical inertness and low coefficient of friction afforded by PTFE.

A length of SILASTIC®Rx50 Silicone Tubing manufactured by Dow Corning Corporation (Midland, Mich.) having an inner diameter of 1.5 mm and an outer diameter of 2.0 mm was fitted coaxially over a 1.1 mm stainless steel mandrel and secured at both ends. The silicone tubing was coated with a thin layer of Translucent RTV 108 Silicone Rubber Adhesive Sealant manufactured by General Electric Company (Waterford, N.Y.). An 8 mm inner diameter film tube made in the same manner described in Example 1 was fitted coaxially over the stainless steel mandrel and the silicone tubing. Tension was manually applied to the ends of the film tube causing it to reduce in diameter and fit snugly onto the underlying segment of silicone tubing secured to the stainless steel mandrel. With the film tube in substantial contact with the silicone tubing, this composite tube was gently massaged to ensure that no voids were present between the silicone tube and the porous PTFE film tube. Next the entire silicone-PTFE composite tube was allowed to cure in an air convection oven set at 35° C. for a minimum of 12 hours. Once cured, the composite tube was removed from the stainless steel mandrel. One end of the composite tube was then fitted coaxially over a section of 5Fr catheter shaft taken from a model B507-412 MATCH 35® Percutaneous Transluminal Angioplasty (PTA) Catheter, manufactured by SCHNEIDER (Minneapolis, Minn.) and clamped to the catheter shaft using a model 03.3 RER Ear Clamp manufactured by Oetiker (Livingston, N.J.) such that a watertight seal was present. The distal end of the balloon was closed using hemostats for expediency, however, a conventional ligature such as waxed thread may be used to provide a suitable closure. In this manner a balloon catheter was fashioned, utilizing the silicone-PTFE composite tube as the balloon material.

At this point, the balloon was measured in a pre-inflated state. The minimum dimension was found to be 2.31 mm and the maximum dimension 2.42 mm. As before, these measurements were taken from approximately the midpoint of the balloon, and a Lasermike model 183, manufactured by Lasermike, (Dayton, Ohio) was used to make the measurements while the balloon was rotated about its longitudinal axis. The balloon, when inflated to 8 atmospheres internal water pressure, had a minimum dimension of 7.64 mm and a maximum dimension of 7.76 mm at the center of the balloon. When deflated by removing the entire volume of water introduced during the 8 atmosphere pressurization, the balloon at its midlength, had a minimum dimension of 2.39 mm and a maximum dimension of 2.57 mm. The silicone-PTFE composite balloon when tested using a hand-held inflation device had a burst strength of 150 psi, reaching a maximum dimension of about 7.9 mm prior to rupture.

This example illustrates that the balloon made from the silicone-PTFE composite tube exhibited a predictable limit to its diametrical growth as demonstrated by the destructive burst strength test wherein the balloon did not exceed the 8 mm diameter of the porous PTFE film tube component. The compaction ratio as previously defined was 2.42÷2.57 or 0.94, and the compaction efficiency ratio as previously defined was 2.39÷2.57, or 0.93.

EXAMPLE 4

This example describes the construction of a PTA balloon made by helically wrapping a porous PTFE film having a non-porous FEP coating over a thin porous PTFE tube.

The FEP-coated porous expanded PTFE film was made by a process which comprises the steps of:
a) contacting a porous PTFE film with another layer which is preferably a film of FEP or alternatively of another thermoplastic polymer;
b) heating the composition obtained in step a) to a temperature above the melting point of the thermoplastic polymer;
c) stretching the heated composition of step b) while maintaining the temperature above the melting point of the thermoplastic polymer; and
d) cooling the product of step c).

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching, and the thickness of the adhesive prior to stretching.

The FEP-coated porous PTFE film used to construct this example was a continuous (non-porous) film. The total thickness of the coated film was about 0.02 mm. The film was helically wrapped onto an 8 mm diameter stainless steel mandrel that had been coaxially covered with a porous expanded PTFE tube, made as taught by U.S. Pat. Nos. 3,953,566 and 4,187,390. The porous PTFE tube was a 3 mm inside diameter tube having a wall thickness of about 0.10 mm and a fibril length of about 30 microns. Fibril length is measured as taught by U.S. Pat. No. 4,972,846. The 3 mm tube had been stretched to fit snugly over the 8 mm mandrel. The FEP-coated porous PTFE film was then wrapped over the outer surface of this porous PTFE tube in the same manner as described by Example 1, with the FEP-coated side of the film placed against the porous PTFE tube surface. The wrapped mandrel was placed into an air convection set at 380° C. for 2.5 minutes, removed and allowed to cool, at which time the resulting tube was removed from the mandrel. One end of this tube was fitted coaxially over the end of a 5Fr catheter shaft taken from a model number B507-412 PTA catheter manufactured by Schneider (Minneapolis, Minn.), and clamped to the catheter shaft using a model 03.3 RER Ear Clamp manufactured by Oetiker (Livingston, N.J.) such that a watertight seal was present. The resulting balloon was packed into the protective sheath which was provided by Schneider as part of the packaged balloon catheter assembly. The balloon was then removed from the protective sheath by sliding the sheath proximally off of the balloon and over the catheter shaft. Prior to inflation, the minimum and maximum diameters of the balloon were determined to be 2.25 and 2.61 mm. The distal end of the balloon was then closed using hemostats for expediency, however, a conventional ligature such as waxed thread could have been used to provide a suitable closure. When inflated to a pressure of 6 atmospheres, the minimum and maximum diameters were 8.43 and 8.49 mm. After being deflated the minimum and maximum diameters were 1.19 and 12.27 mm. These diameters resulted in a compaction ratio of 0.21 and a compaction efficiency of 0.10.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:
1. A balloon catheter having a balloon comprised of porous polytetrafluoroethylene and an elastomeric material, said balloon having a longitudinal axis, said porous polytetrafluoroethylene comprising a film oriented helically with respect to said longitudinal axis.

2. A balloon catheter according to claim 1 wherein said balloon following inflation to 5 atmospheres and subsequent deflation has a compaction efficiency ratio of greater than about 0.3.

3. A balloon catheter according to claim 2 wherein said balloon following inflation to 5 atmospheres and subsequent deflation has a compaction efficiency ratio of greater than about 0.7.

4. A balloon catheter according to claim 3 wherein said balloon following inflation to 5 atmospheres and subsequent deflation has a compaction efficiency ratio of greater than about 0.9.

5. A balloon catheter according to claim 1 wherein the elastomeric material is selected from the group consisting of fluoroelastomers, silicone rubbers, latex rubbers and polyurethanes.

6. A balloon catheter according to claim 1 wherein said balloon following inflation to 5 atmospheres and subsequent deflation has a compaction ratio of greater than about 0.5.

7. A balloon catheter according to claim 6 wherein said balloon following inflation to 5 atmospheres and subsequent deflation has a compaction ratio of greater than about 0.6.

8. A balloon catheter according to claim 1 wherein the balloon resists appreciable distension beyond a maximum diameter.

9. A balloon catheter according to claim 8 wherein the balloon has a burst pressure of at least about 70 psi.

10. A balloon catheter according to claim 9 wherein the balloon has a burst pressure of at least about 100 psi.

11. A balloon catheter according to claim 1 wherein the polytetrafluoroethylene is a cover that fits over the elastomeric material.

12. A balloon catheter according to claim 1 wherein the porous polytetrafluoroethylene has pores that are substantially filled with elastomeric material.

13. A balloon catheter having a balloon comprised of polytetrafluoroethylene and an inelastic material.

14. A balloon catheter according to claim 13 wherein the inelastic material is a fluoropolymer.

15. A balloon catheter according to claim 13 wherein said balloon following inflation to 5 atmospheres and subsequent deflation has a compaction ratio of greater than about 0.4.

16. A balloon catheter according to claim 15 wherein said balloon following inflation to 5 atmospheres and subsequent deflation has a compaction ratio of greater than about 0.6.

17. A balloon catheter according to claim 13 wherein the balloon resists appreciable distension beyond a maximum diameter.

18. A balloon catheter according to claim 13 wherein the polytetrafluoroethylene is a cover that fits over the inelastic material.

19. A balloon catheter according to claim 13 wherein the porous polytetrafluoroethylene has pores that are substantially filled with elastomeric material.

20. A balloon catheter according to claim 13 wherein said balloon following inflation to 5 atmospheres and subsequent deflation has a compaction efficiency ratio of greater than about 0.3.

21. A balloon catheter according to claim 20 wherein said balloon following inflation to 5 atmospheres and subsequent deflation has a compaction efficiency ratio of greater than about 0.5.

22. A balloon catheter according to claim 21 wherein said balloon following inflation to 5 atmospheres and subsequent deflation has a compaction efficiency ratio of greater than about 0.7.

23. A balloon catheter having a balloon provided with a balloon cover, said cover comprised of polytetrafluoroethylene and an elastomeric material and having a generally tubular form selected from the group consisting of continuous tubes, meshes or braids.

24. A balloon catheter having a balloon provided with a balloon cover, said cover comprised of polytetrafluoroethylene having a generally tubular form selected from the group consisting of continuous tubes, meshes or braids.

25. A catheter balloon comprising expanded polytetrafluoroethylene and elastomer;

the expanded polytetrafluoroethylene and elastomer connected to an inflation means to form the balloon;

the balloon having an initial deflated diameter and an inflated maximum diameter;

wherein the expanded polytetrafluoroethylene and the elastomer inflate together to reach the maximum diameter and the expanded polytetrafluoroethylene and the elastomer contract together when the balloon is deflated wherein the balloon recovers to substantially the initial deflated diameter.

26. A catheter balloon according to claim 25 wherein the expanded polytetrafluoroethylene and elastomer are laminated together.

27. A catheter balloon according to claim 25 wherein the elastomer is impregnated into at least a portion of void spaces in the expanded polytetrafluoroethylene.

28. A catheter balloon according to claim 27 wherein the elastomer substantially fills void spaces in the expanded polytetrafluoroethylene.

29. A catheter balloon according to claim 25 wherein the expanded polytetrafluoroethylene and elastomer are laminated together and wherein the elastomer is also impregnated into at least a portion of void spaces in the expanded polytetrafluoroethylene.

30. A catheter balloon comprising polytetrafluoroethylene and an elastomer;

inflation means connected to the balloon;

the polytetrafluoroethylene, elastomer, and inflation means combining to form the balloon which is fluid-tight with a high burst strength of at least 8 atmospheres;

wherein the balloon has an initial deflated diameter and a maximum inflated diameter; and wherein the balloon is capable of being inflated to its maximum diameter and then deflated to substantially its initial deflated diameter.

31. A catheter balloon according to claim 30 wherein the polytetrafluoroethylene and elastomer are laminated together.

32. A catheter balloon according to claim 30 wherein the polytetrafluoroethylene is porous and contains void spaces and wherein the elastomer is impregnated into at least a portion of the void spaces in the polytetrafluoroethylene.

33. A catheter balloon according to claim 32 wherein the elastomer substantially fills void spaces in the polytetrafluoroethylene.

34. A catheter balloon according to claim 30 wherein the polytetrafluoroethylene and elastomer are laminated together and wherein the elastomer is also impregnated into at least a portion of void spaces contained in the polytetrafluoroethylene.

35. A catheter balloon comprising polytetrafluoroethylene and an elastomeric material;

wherein the balloon has an Initial deflated diameter and a maximum inflated diameter; and wherein the balloon is capable of being inflated to its maximum diameter and then deflated to substantially its initial deflated diameter.

36. A catheter balloon comprising polytetrafluoroethylene and an elastomeric material;

wherein said polytetrafluoroethylene further comprises a helical wrapping of polytetrafluoroethylene film.

37. A catheter balloon comprising porous material and elastomeric material;

wherein the porous material include void spaces, said void spaces being sealed with elastomeric material to render the balloon liquid-tight.

38. A catheter balloon comprising polytetrafluoroethylene and elastomeric material;

said balloon being liquid-tight.

* * * * *